United States Patent [19]

Hsia et al.

[11] Patent Number: 4,479,812
[45] Date of Patent: Oct. 30, 1984

[54] SORPTION FRACTIONATION SYSTEM FOR OLEFIN SEPARATION

[75] Inventors: Chung H. Hsia, Matawan; Hartley Owen, Belle Mead; Bernard S. Wright, East Windsor, all of N.J.

[73] Assignee: Mobil Oil Corporation, New York, N.Y.

[21] Appl. No.: 508,779

[22] Filed: Jun. 29, 1983

[51] Int. Cl.$^3$ .......................... B01D 47/12; B01D 3/16
[52] U.S. Cl. .......................................... 55/48; 55/51; 55/94; 203/42; 208/341
[58] Field of Search .................... 55/50, 65, 80, 88, 94, 55/223, 48, 51; 203/42; 208/341, 342, 349, 350

[56] References Cited

U.S. PATENT DOCUMENTS

| | | | |
|---|---|---|---|
| 2,181,302 | 11/1939 | Keith, Jr. et al. | 196/10 |
| 2,577,617 | 12/1951 | Hudig | 62/175.5 |
| 2,905,734 | 9/1959 | Davison et al. | 260/683 |
| 2,938,865 | 5/1960 | Moyer | 208/341 |
| 2,939,834 | 6/1960 | Evans | 208/342 X |
| 3,160,582 | 12/1964 | Cabbage | 208/361 |
| 3,421,610 | 1/1969 | Marshall | 208/341 X |
| 3,537,978 | 11/1970 | Borst | 208/341 X |
| 3,542,892 | 11/1970 | Stoker et al. | 208/342 X |
| 3,607,734 | 9/1971 | Stafford | 208/341 |

FOREIGN PATENT DOCUMENTS

0566596 3/1975 U.S.S.R. ............................... 203/42

Primary Examiner—Charles Hart
Attorney, Agent, or Firm—A. J. McKillop; M. G. Gilman; L. G. Wise

[57] ABSTRACT

A continuous fractionation technique is provided for recovering ethylene from an olefinic feedstock comprising $C_3^+$ higher olefins. This technique provides methods and means for contacting the olefinic feedstock in a counter current sorption tower with a liquid sorbent stream comprising $C_6^+$ gasoline range hydrocarbons under process conditions to selectively sorb substantially the entire $C_3^+$ olefin components from the feedstock, withdrawing an ethylene-rich vapor stream from the sorption tower and further contacting the ethylene-rich stream with a distillate range liquid hydrocarbon stream in a sponge absorber to purify the ethylene stream. Typically, the olefinic feedstock consists essentially of volatile hydrocarbons, and preferably comprises about 10 to 50 mole % ethylene and 10 to 50 mole % propene. Purified ethylene product may be recovered having an average molecular weight not greater than 28.5 under non-cryogenic conditions.

5 Claims, 1 Drawing Figure

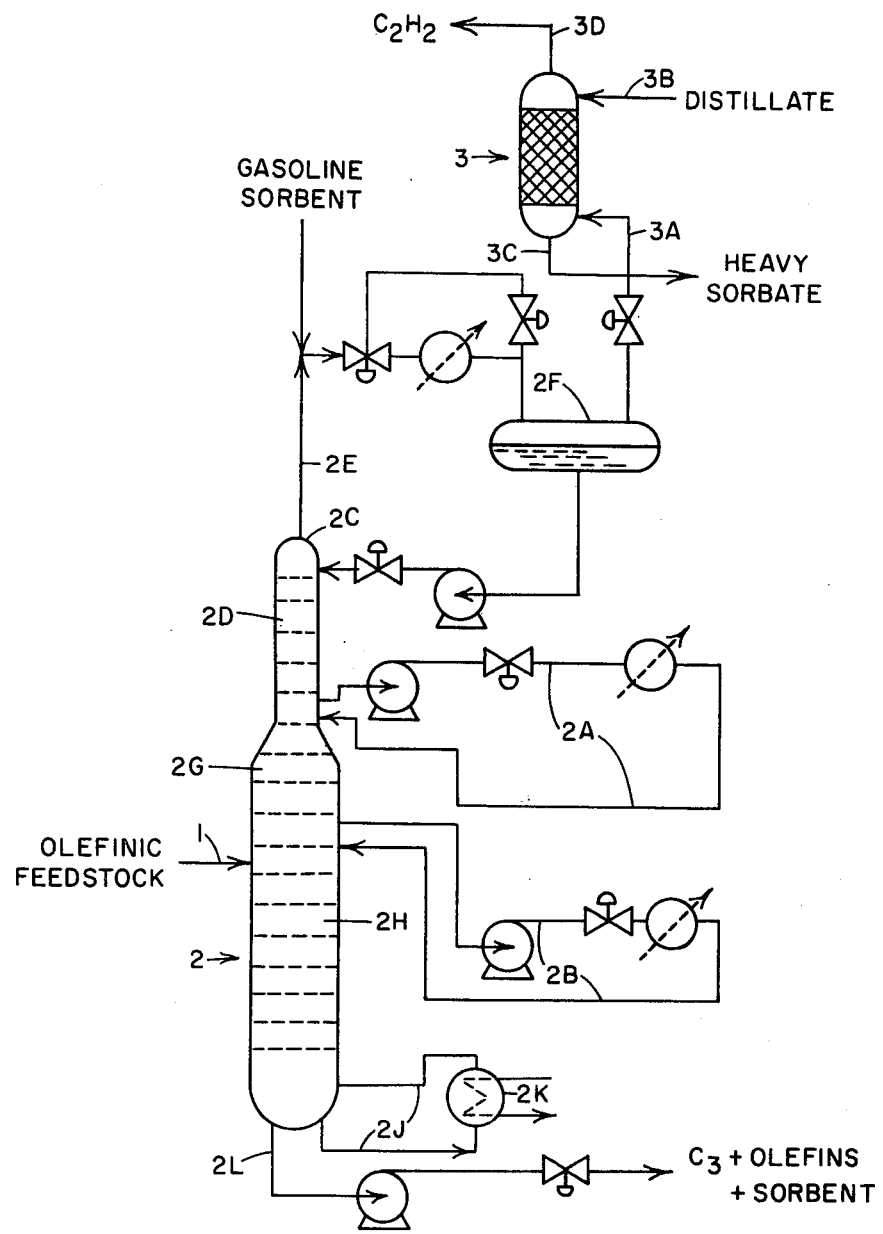

SORPTION FRACTIONATION SYSTEM FOR OLEFIN SEPARATION

FIELD OF THE INVENTION

This invention relates to a technique for separating light olefins to recover ethylene. In particular it relates to a novel system for fractionating an olefinic feedstock containing $C_2$ and $C_3+$ olefins in mixture.

BACKGROUND OF THE INVENTION

In the refining of petroleum or manufacture of fuels from fossil materials or various sources of hydrocarbonaceous sources, an olefinic mixture is often produced. For instance, in cracking heavier petroleum fractions, such as gas oil, to make gasoline or distillate range products, light gases containing ethene, propene, butene and related aliphatic hydrocarbons are produced. It is known to recover these valuable dry-products for use as chemical feedstocks for other processes, such as alkylation, polymerization, oligomerization, LPG fuel, etc. Ethylene is particularly valuable as a basic material in the manufacture of polyethylene and other plastics, and its commercial value is substantially higher as a precursor for the chemical industry than as a fuel component. Accordingly, it is desirable to separate ethylene in high purity for such uses.

A typical byproduct of fluid catalytic cracking (FCC) units is an olefinic stream rich in $C_2$–$C_4$ olefins, usually in mixture with lower alkanes. Ethylene can be recovered from such streams by conventional fractionation means, such as cryogenic distillation, to recover the $C_2$ and $C_3+$ fractions; however, the equipment and processing costs are high. It is an object of the present invention to provide a novel process and apparatus for separating ethylene from olefinic mixtures economically.

SUMMARY OF THE INVENTION

It has been found that propylene and other $C_3+$ aliphatic hydrocarbons can be separated efficiently from a mixture of volatile hydrocarbons, typically containing a major fraction of $C_2$–$C_5$ olefins, by absorption in a multi-stage sorption system utilizing heavier liquid hydrocarbon sorbants. $C_6+$ olefinic gasoline is effective in absorbing propylene and higher molecular weight aliphatics from ethylene and other light gases by selective sorption. This technique is employed in a fractionating absorption system for recovering ethene from a hydrocarbon feedstock mixture comprising $C_2$–$C_5$ olefins employing a countercurrent gas-liquid contact tower having an upper liquid sorbent inlet means for supplying $C_6+$ gasoline range hydrocarbons, gaseous feedstock inlet, lower liquid outlet and an upper gas outlet for unabsorbed ethene rich vapors. In a separate stage operatively connected to receive ethene-rich vapors from the feedstock contact tower, a sponge absorber-type contact means is provided for absorbing $C_3+$ hydrocarbons from the ethene-rich vapors, thereby producing high purity ethene product. In a preferred embodiment of the fractionating system, the sponge absorber includes a distillate heavy hydrocarbon liquid stream and a packed column for contacting vapors countercurrently with the liquid stream and means for withdrawing heavy liquid hydrocarbons with sorbed $C_3+$ hydrocarbons.

The sorption process may be operated under non-cryogenic conditions at moderate pressure and temperature using gasoline range hydrocarbons consisting essentially of $C_6$ to $C_{10}$ aliphatics.

THE DRAWING

The drawing is a process diagram showing a typical sorption system with hydrocarbon streams.

DESCRIPTION OF PREFERRED EMBODIMENTS

The present system is adapted to separate volatile hydrocarbons comprising a major amount of $C_2$–$C_4$ olefins, and typically contains 10 to 50 mole % of ethene and propene each. In the detailed examples herein the feedstock consists essentially of volatile aliphatic components as follows: ethene, 24.5 mole %, propene, 46%; propane, 6.5%; 1-butene, 15% and butanes 8%, heaving an average molecular weight of about 42 and more than 85 mole % olefins.

The gasoline sorbent is an aliphatic hydrocarbon mixture boiling in the normal gasoline range of about 50° to 165° C. (125° to 330° F.), with minor amounts of $C_4$–$C_5$ alkanes and alkenes. Preferably, the total gasoline sorbent stream to feedstock weight ratio is greater than about 3:1; however, the content of $C_3+$ olefinic components in the feedstock is a more preferred measure of sorbate to sorbent ratio. Accordingly, the process may be operated with a mole ratio of about 0.2 moles to about 10 moles of gasoline per mole of $C_3+$ hydrocarbons in the feedstock, with optimum operation utilizing a sorbent:sorbate molar ratio about 1:1 to 1.5:1.

It is understood that the various process conditions are given for a continuous system operating at steady state, and that substantial variations in the process are possible within the inventive concept. In the detailed examples, metric units and parts by weight are employed unless otherwise specified.

Referring to the drawing, olefinic feedstock is introduced to the system through a feedstock inlet 1 connected between stages of a fractionating sorption tower 2 wherein gaseous olefinic feedstock is contacted with liquid sorbent in a vertical fractionation column operating at least in the upper portion thereof in countercurrent flow. Effectively this unit is a $C_2/C_3+$ splitter. Design of sorption equipment and unit operations are established chemical engineering techniques, and generally described in Kirk-Othmer "Encyclopedia of Chemical Technology" 3rd Ed. Vol. 1 pp. 53–96 (1978) incorporated herein by reference. In conventional refinery terminology, the sorbent stream is sometimes known as lean oil.

Sorption tower 2, as depicted, has multiple contact zones, with the heat of absorption being removed via interstage pump around cooling means 2A, 2B. The liquid gasoline sorbent is introduced to the sorption tower through an upper inlet means 2C above the top contact section 2D. It is preferred to mix incoming liquid sorbent with outgoing splitter overhead ethylene-rich gas from upper gas outlet 2E and to pass this multiphase mixture into a phase separator 2F, operatively connected between the primary sorption tower 2 and a secondary sponge absorber 3. Liquid sorbent from separator 2F is then pumped to the upper liquid inlet 2C for countercurrent contact in a plate column or the like with upwardly flowing ethylene rich vapors. Liquid from the bottom of upper contact zone 2D is pumped to a heat exchanger in loop 2A, cooled and returned to the tower above intermediate contact zone 2G, again cooled in loop 2B, and returned to the tower above contact zone 2H, which is located below the feedstock inlet 1. Under tower design conditions of about 2100 kPa (300 psia), it is preferred to maintain liquid temperature of streams entering the tower from 2A, 2B and 2F at about 40° C. (100° F.). The lower contact zone 2H provides further fractionation of the olefin-rich liquid. Heat is supplied to the sorption tower by removing liquid from the bottom via reboiler loop 2J, heating this stream in heat exchanger 2K, and returning the reboiled bottom stream to the tower below contact zone 2H.

The liquid sorbate-sorbent mixture is withdrawn through bottom outlet 2L and pumped to storage or to olefins recovery or to reaction. This stream is suitable for use as a feedstock in an olefins oligomerization unit or may be utilized as fuel products. Ethylene rich vapor from the primary sorption tower is withdrawn via separator 2F through conduit 3A.

Distillate lean oil is fed to the top inlet 3B of sponge absorber 3 under process pressure at ambient or moderately warm temperature (eg. 40° C.) and distributed at the top of a porous packed bed, such as Raschig rings, having sufficient bed height to provide multiple stages. The liquid rate is low; however, the sponge absorber permits sorption of about 25 wt. percent of the distillate weight in $C_3^+$ components sorbed from the ethylene-rich stream. This stream is recovered from bottom outlet 3C. It is understood that the sorbate may be recovered from mixture with the sorbent by fractionation and the sorbent may be recycled or otherwise utilized. High purity ethylene is recovered from the system through gas outlet 3D and sent to storage, further processing or conversion to other products.

The sorption towers depicted in the drawing employ a plate column in the primary tower and a packed column in the secondary tower, however, the fractionation equipment may employ vapor-liquid contact means of various designs in each stage including packed beds of Raschig rings, saddles or other porous solids or low pressure drop valve trays (Glitsch grids). The number of theoretical stages will be determined by the feed-stream composition, liquid:vapor (L/V) ratios, desired recovery and product purity. In the detailed example herein, 17 theoretical stages are employed in the primary sorption tower and 8 stages in the sponge absorber, with olefinic feedstock being fed between the 7th and 9th stages of the primary sorption tower.

primary sorption tower, and Table II shows the conditions for the sponge absorber units for Example 1 (2 moles gasoline/mole of olefin in feedstock).

TABLE I

| Stage | Heat In KW/MT | Temperature (°C.) | Liquid/Vapor (L/V) Mole Ratio | Pressure (kPa) |
|---|---|---|---|---|
| 1 (top) | −121. + 362[1] | 37.8 | 6.947 | 2068.5 |
| 2 | | 38.5 | 2.245 | 2103.0 |
| 3 | | 39.7 | 2.222 | 2103.7 |
| 4 | | 42.3 | 2.227 | 2104.4 |
| 5 | | 47.2 | 2.221 | 2105.1 |
| 6 | | 54.2 | 2.185 | 2105.8 |
| 7 | −29.[2] | 57.6 | 2.216 | 2106.5 |
| 8 | | 65.3 | 1.864 | 2107.2 |
| 9 | −820. + 120[3] | 59.9 | 2.447 | 2107.9 |
| 10 | | 67.7 | 1.954 | 2108.6 |
| 11 | | 71.8 | 1.814 | 2109.3 |
| 12 | | 74.1 | 1.743 | 2110.0 |
| 13 | | 75.4 | 1.704 | 2110.7 |
| 14 | | 77.0 | 1.684 | 2111.4 |
| 15 | | 80.5 | 1.644 | 2112.1 |
| 16 | | 92.3 | 1.541 | 2112.8 |
| 17 (bottom) | 400.[4] | 136.2 | 0.872 | 2116.3 |

[1] Condenser Duty & Lean Oil
[2] 1st Heat Removal Duty
[3] 2nd Heat Removal Duty & Lean Oil
[4] Reboiler Duty, based on metric tons (MT) of feedstock

TABLE II

| Stage | Heat In (KW/MT) | Temperature (°C.) | Liquid/Vapor (L/V) Mole Ratio | Pressure (kPa) |
|---|---|---|---|---|
| 1 | 2.9[1] | 42.8 | 0.045 | 1999.6 |
| 2 | | 42.3 | 0.046 | 2000.2 |
| 3 | | 41.8 | 0.046 | 2000.9 |
| 4 | | 41.4 | 0.047 | 2001.6 |
| 5 | | 41.2 | 0.047 | 2002.3 |
| 6 | | 40.9 | 0.048 | 2003.0 |
| 7 | | 40.6 | 0.050 | 2003.7 |
| 8 | 32.8[2] | 40.1 | 0.056 | 2004.4 |

[1] Distillate Lean Oil
[2] $C_2^=/C_3^+$ Splitter Overhead

Based on the above design, the following data show the effects of varying the flow rate of gasoline absorbent in the primary tower $C_2/C_3^+$ splitter overhead and the corresponding effects of varying the distillate lean oil rate in the secondary sponge absorber. These data are shown in Table III, which give the ethylene ($C_2^=$) recovery and purity from each of the primary and secondary sprotion units.

TABLE III

| Example No. | Gasoline Mole Ratio [1] | Distillate Mole Ratio | C2/C3+ Splitter Overhead | | | Sponge Absorber Overhead | | |
|---|---|---|---|---|---|---|---|---|
| | | | C2= Recovery % | C2= Purity MOL % | WT % | C2= Recovery % | C2= Purity MOL % | WT % |
| 1 | 2:1 | 0.013 | 99.92 | 98.21 | 95.24 | 98.37 | 99.18 | 97.91 |
| 2 | 1:1 | 0.013 | 99.94 | 85.16 | 77.74 | 98.32 | 86.43 | 78.39 |
| 3 | 1.5:1 | 0.013 | 99.93 | 96.43 | 92.56 | 98.37 | 97.45 | 95.53 |
| 4 | 3:1 | 0.013 | 99.90 | 98.40 | 95.46 | 98.35 | 99.36 | 98.16 |
| 5 | 4:1 | 0.013 | 99.88 | 98.42 | 95.45 | 98.32 | 99.39 | 98.40 |
| 6 | 2:1 | 0.006 | 99.92 | 98.21 | 95.24 | 99.02 | 98.98 | 97.48 |
| 7 | 2:1 | 0.01 | 99.92 | 98.21 | 95.24 | 98.68 | 99.09 | 97.67 |
| 8 | 2:1 | 0.019 | 99.92 | 98.21 | 95.24 | 97.77 | 99.31 | 98.40 |
| 9 | 2:1 | 0.025 | 99.92 | 98.21 | 95.24 | 97.17 | 99.43 | 98.65 |

[1] Gasoline Absorbent Rate Moles/Mole of Total Olefin in Feedstock.

Examples 1 to 9 are based on the above-described feedstock at 40° C. (100° F.) and 2100 kPa (300 psia) supplied to stage 9 of the primary sorption tower. Gasoline is supplied at 85° C. (185° F.) and 2150 kPa (305 psia), and distillate lean oil is supplied at 40° C. and 2100 kPa. Table I shows the conditions at each stage of the In general, as the flow rate of lean oil increases, the ethylene recovery decreases, while the purity increases. The data for the splitter/absorber combination show that the excellent results are obtained with a gasoline mole ratio of at least 1:1 (based on $C_3^+$ hydrocarbons).

Such conditions will result in a $C_2^=$ recovery of greater than 98%. Purity of more than 99 mole % can be achieved with a gasoline mole ratio of at least 2:1.

A preferred sorbent source is olefinic gasoline and distillate produced by catalytic oligomerization according to U.S. Pat. No. 4,211,640 (Garwood & Lee) and U.S. patent application Ser. No. 488,834, filed Apr. 26, 1983 (Owen et al), incorporated herein by reference. The $C_3+$ olefin sorbate and gasoline may be fed directly to such oligomerization process, with a portion of recovered gasoline and distillate being recycled to the sorption fractionation system herein. Table IV shows the boiling range fraction composition for typical gasoline and distillate sorbents.

TABLE IV

| Lean Oil Compositions (MOL %) | | |
| --- | --- | --- |
|  | Gasoline | Distillate |
| Propane | 0.00 | 0 |
| Isobutane | 0.15 | 0 |
| 1-Butene | 0.12 | 0 |
| N—Butene | 0.59 | 0 |
| Isopentane | 2.60 | 0 |
| 1-Pentene | 0.24 | 0 |
| N—Pentane | 0.24 | 0 |
| 52–82° C. | 11.24 | 0 |
| 82–104° C. | 22.02 | 0 |
| 104–127° C. | 23.54 | 0.02 |
| 127–138° C. | 11.23 | 0.09 |
| 138–149° C. | 10.47 | 0.43 |
| 149–160° C. | 8.70 | 2.00 |
| 160–171° C. | 1.54 | 2.13 |
| 171–182° C. | 0.92 | 7.06 |
| 182–193° C. | 0.31 | 11.16 |
| 193–204° C. | 0.10 | 14.53 |
| 204–216° C. | 0.01 | 8.36 |
| 216–227° C. | 0.00 | 8.56 |
| 227–238° C. | 0 | 7.56 |
| 238–249° C. | 0 | 6.50 |
| 249–260° C. | 0 | 6.00 |
| 260–271° C. | 0 | 4.30 |
| 271–293° C. | 0 | 5.10 |
| 293–316° C. | 0 | 4.13 |
| 316–338° C. | 0 | 3.24 |
| 338–360° C. | 0 | 3.17 |
| 360–382° C. | 0 | 4.63 |
| 382–404° C. | 0 | 0.91 |
| 404–438° C. | 0 | 0.11 |

The sponge absorber may be constructed in a separate unit, as shown, or this operation may be conducted in an integral shell vessel with the main fractionation unit. In the alternative integral design, the rich sponge oil may be recovered from the upper contact zone as a separate stream, or the heavy distillate sorbent may be intermixed downwardly with gasoline sorbent and withdrawn from the bottom of the main fractionation zone.

While the invention has been described by specific examples and embodiment, there is no intent to limit the inventive concept except as set forth in the following claims.

What is claimed is:

1. A continuous fractionation process for recovering ethylene from an olefinic feedstock comprising about 10 to 50 mole % ethylene and 10 to 50 mole % propene, said olefinic feedstock consisting essentially of volatile $C_2$–$C_4$ hydrocarbons comprising the steps of
    contacting the olefinic feedstock in a countercurrent sorption tower with a liquid sorbent stream comprising $C_6+$ olefinic gasoline range hydrocarbons under process conditions to selectively sorb substantially the entire $C_3+$ olefin components from the feedstock;
    withdrawing an ethylene-rich vapor stream from the sorption tower; and
    further contacting the ethylene-rich stream with a distillate range liquid hydrocarbon stream in a sponge absorber to recover ethylene having an average molecular weight not greater than 28.5.

2. The process of claim 1 wherein olefinic liquid gasoline sorbent is supplied to the sorption tower as a molar ratio of about 0.2:1 to 10:1 based on feedstock $C_3+$ olefins.

3. The process of claim 2 wherein the distillate liquid stream is supplied to the sponge absorber at a molar ratio of about 0.1:1 to 0.06:1 based on ethylene whereby $C_3+$ and gasoline range hydrocarbons escaping the first sorption tower with the ethylene rich stream are absorbed by the distillate liquid.

4. The process of claim 1 wherein fractionation is conducted under non-cryogenic conditions and process pressure is maintained at about 2000 to 2200 kPa.

5. A continuous fractionation process for recovering ethylene from an olefinic feedstock comprising about 10 to 50 mole % ethylene and 10 to 50 mole % propene, said olefinic feedstock consisting essentially of volatile $C_2$–$C_4$ hydrocarbons; comprising the steps of
    contacting the olefinic feedstock in a countercurrent sorption tower with a liquid sorbent stream comprising $C_6+$ olefinic gasoline range hydrocarbons under process conditions to selectively sorb substantially the entire $C_3+$ olefin components from the feedstock;
    withdrawing an ethylene-rich vapor stream from the sorption tower;
    mixing the ethylene-rich vapor with incoming liquid sorbent and passing the mixture thereof into a phase separator operatively connected between the sorption tower and a sponge absorber;
    passing liquid sorbent from the phase separator to the countercurrent sorption tower; and
    further contacting the ethylene-rich stream with a distillate range liquid hydrocarbon stream in the sponge absorber to recover substantially pure ethylene.

* * * * *